(12) United States Patent
Kim

(10) Patent No.: US 6,984,405 B1
(45) Date of Patent: Jan. 10, 2006

(54) COMPOSITIONS FOR INDUCING SECRETION OF INSULIN-LIKE GROWTH FACTOR-1

(75) Inventor: Jae-Soo Kim, Seoul (KR)

(73) Assignee: Naturalendo Tech Co., Ltd. (KR)

( * ) Notice: Subject to any disclaimer, the term of this patent is extended or adjusted under 35 U.S.C. 154(b) by 127 days.

(21) Appl. No.: 10/450,545

(22) PCT Filed: Dec. 14, 2001

(86) PCT No.: PCT/KR01/02170

§ 371 (c)(1),
(2), (4) Date: Jun. 13, 2003

(87) PCT Pub. No.: WO02/47702

PCT Pub. Date: Jun. 20, 2002

(30) Foreign Application Priority Data

| Dec. 15, 2000 | (KR) | 2000/77121 |
| Sep. 10, 2001 | (KR) | 2001-55519 |
| Oct. 22, 2001 | (KR) | 2001/65100 |

(51) Int. Cl.
*A61K 35/78* (2006.01)

(52) U.S. Cl. .................. 424/725; 424/439
(58) Field of Classification Search ............ 424/725, 424/439
See application file for complete search history.

(56) References Cited

U.S. PATENT DOCUMENTS

| 5,240,961 A | 8/1993 | Shuhg |
| 5,466,670 A | 11/1995 | Dunger et al. |
| 5,861,373 A | 1/1999 | Gluckman et al. |
| 5,985,924 A | * 11/1999 | Ishikawa et al. |

FOREIGN PATENT DOCUMENTS

| CN | 1140593 A | 1/1997 |
| CN | 1218628 A | 6/1999 |
| JP | 07-025777 A | 1/1995 |
| SU | 904710 B | 2/1982 |

OTHER PUBLICATIONS

CAPLUS English abstract of Liu et al. (Zhongcaoyao (1999), vol. 30, No. 3, pp. 161–164).*

International Search Report—PCT/KR01/02170; ISA/Austrian Patent Office, Mar. 1, 2002.

* cited by examiner

Primary Examiner—Susan D. Coe
(74) Attorney, Agent, or Firm—Harness, Dickey & Pierce, P.L.C.

(57) ABSTRACT

The present invention relates to a pharmaceutical or a food composition for inducing or stimulating secretion of insulin-like growth factor-1. More particularly, the present invention relates to compositions for inducing or stimulating secretion of insulin-like growth factor-1, which comprises (a) a pharmaceutically effective amount of an extract obtained from oriental pharmaceutical selected from the group consisting of *Phlomis umbrosa Turcz, Cynanchum wilfordii(Max) Hem≦, Zingiber officinale Rosc., Platycodi Radix* and combination thereof; and (b) a pharmaceutical acceptable carrier.

7 Claims, 7 Drawing Sheets

COMPOSITIONS FOR INDUCING SECRETION OF INSULIN-LIKE GROWTH FACTOR-1

BACKGROUND OF THE INVENTION

1. Field of the Invention

The present invention relates to a composition for inducing or stimulating secretion of insulin-like growth factor-1. More particularly, the present invention relates to a pharmaceutical or a food composition for inducing or stimulating secretion of insulin-like growth factor-1.

2. Description of the Related Art

Insulin-like growth factor (hereinafter referred to as "IGF-1") consists of single chain polypeptides containing 70 amino acids, which is primarily secreted in liver. IGF-1 exhibits its physiological function by virtue of IGF-1 receptor. Numerous studies have been performed for the physiological function of IGF-1, and as a result, various functions of IGF-1 such as promotion of protein biosynthesis, lowering blood sugar level and facilitation of cell differentiation have been revealed.

For example, it has been reported that IGF-1 is necessary for neural stem cell proliferation and low IGF-1 levels in older women is directly associated with poor muscle strength and mobility. It is demonstrated that administration of IGF-1 is able to regenerate skeletal muscle. In addition, ethanol abuse in alcoholics may lead to decreased IGF-1 bioavailability. IGF-1 is also pivotal in cell proliferation and exhibits treatment effect in diabetic patient (Types 1 and 2) (Thraikill K M, *Diabetes Technol Ther.*, 2(1):69–80(2000)).

It has been revealed that low serum concentrations of IGF-1 are associated with femoral bone loss in a population-based sample of postmenopausal women and IGF-1 is markedly reduced in the acute phase of myocardial infarction. IGF-1 also has been proved to have a protection ability to lesion resulted from ischemiareperfusion in several organ and to prevent neural cells from apoptosis.

As described in Woods K. A. et al., *N. Engl. J. Med.*, 335:1363(1996), patients with IGF-1 deficiency suffers from pre- and postnatal growth failure, mental retardation, microcephaly, and sensorineural deafness and such patients have an inability to produce IGF-1 either locally or systemically while elevated growth hormone secretion combined with an intact growth hormone signaling pathway is observed. Administration of IGF-1 to patients with IGF-1 deficiency is responsible for improvement of body composition, insulin sensitivity, bone mineral density and linear growth (K. A. Woods. et al., *J. Clin. Endocri. & Met.*, 85:1407(2000)).

Furthermore, according to Blum et al. (*J. Clin. Endocrinol. Metab.* 76:1610–1616(1993)), young man who has a low level of IGF-1 and IGF binding protein 3 (IGFBP-3) usually shows shorter height, and Ranke et al., *Horm. Res.* 44: 253–264 (1995) discusses that long-term therapy with IGF-1 is very effective in increasing the rate of linear growth. Namely, IGF-1 is very useful in treatment of patients suffering from deficiency of growth hormone.

As described above, IGF-1 represents various physiological function in cooperative manner with growth hormone or independent manner.

U.S. Pat. No. 5,240,961 discloses methods of treating reduced insulin-like growth factor levels and bone loss associated with aging which include administering L-carnitine and/or its precursors thereof. U.S. Pat. No. 5,466,670 discloses a method for treating Type 1 diabetes mellitus by subcutaneously administering to a patient suffering from Type 1 diabetes mellitus, IGF-1 in a dose effective to achieve an IGF-1 serum level of up to 400 ng/ml that is characteristic in healthy individuals.

In addition, U.S. Pat. No. 5,861,373 discloses a method of treating neural damage suffered after a CNS insult affecting glia or other non-cholinergic cells in a mammal, comprising administering to the central nervous system of said mammal a medicament comprising an effective amount of IGP-1 and/or a biologically active analog of IGF-1.

Hitherto, the effective substances or compositions capable of increasing IGF-1 level in body have not been developed.

Therefore, there is a long-felt need to develop substances or compositions for treating patients suffering from IGF-1 deficiency.

Throughout this application, various patents and publications are referenced and citations are provided in parentheses. The disclosure of these patents and publications in their entities are hereby incorporated by references into this application in order to more fully describe the present invention and the state of the art to which this invention pertains.

SUMMARY OF THE INVENTION

Under such circumstances, the inventor has made intensive study to develop effective substances or compositions capable of increasing IGF-1 level in body. As a result, the inventor has found that extracts from several oriental pharmaceuticals is very effective in inducing or stimulating secretion of IGF-1.

Accordingly, it is an object of this invention to provide a pharmaceutical composition for treating or preventing a disorder associated with reduced serum insulin-like growth factor-1 level.

It is another object of this invention to provide a food composition for inducing secretion of insulin-like growth factor-1.

Other objects and advantages of the present invention will become apparent from the detailed description to follow taken in conjugation with the appended claims and drawings.

DETAILED DESCRIPTION OF THIS INVENTION

Figure 1A:
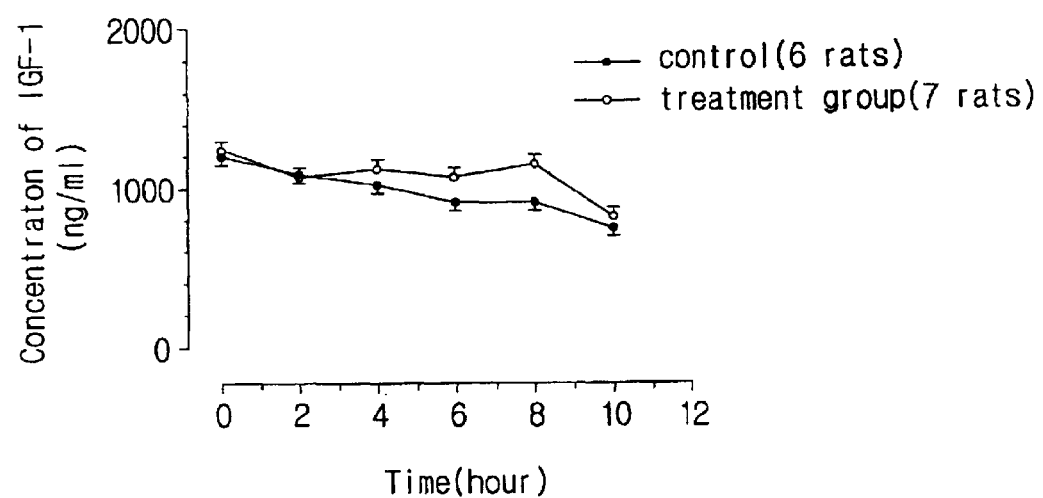
FIGS. 1a–1d are graphs representing the alteration of concentration of IGF-1 in serum by means of compositions comprising the extracts from *Phlomis umbrosa Turez, Cynanchum wilfordii(Max) Hem&ley, Zingiber officinale Rosac.* and *Platycodi Radix*, respectively.
Figure 1B:
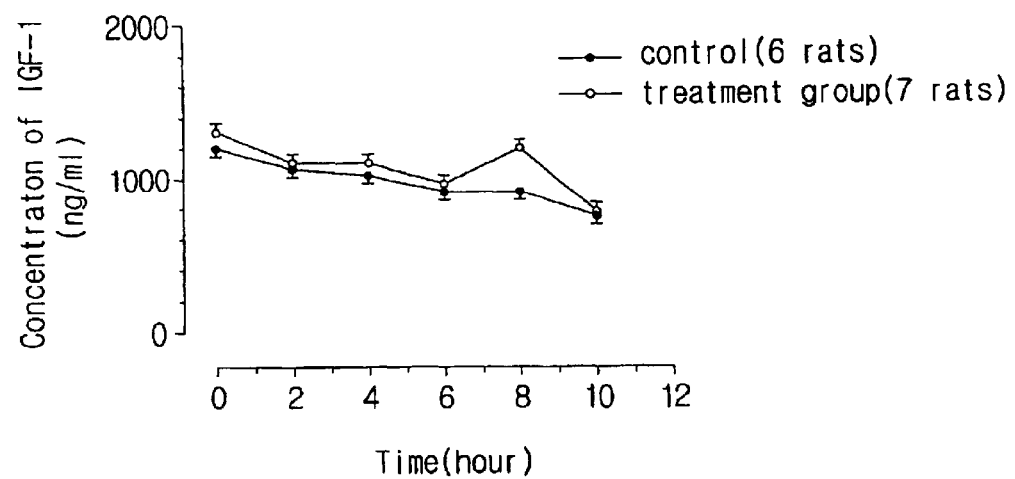
Figure 1C:
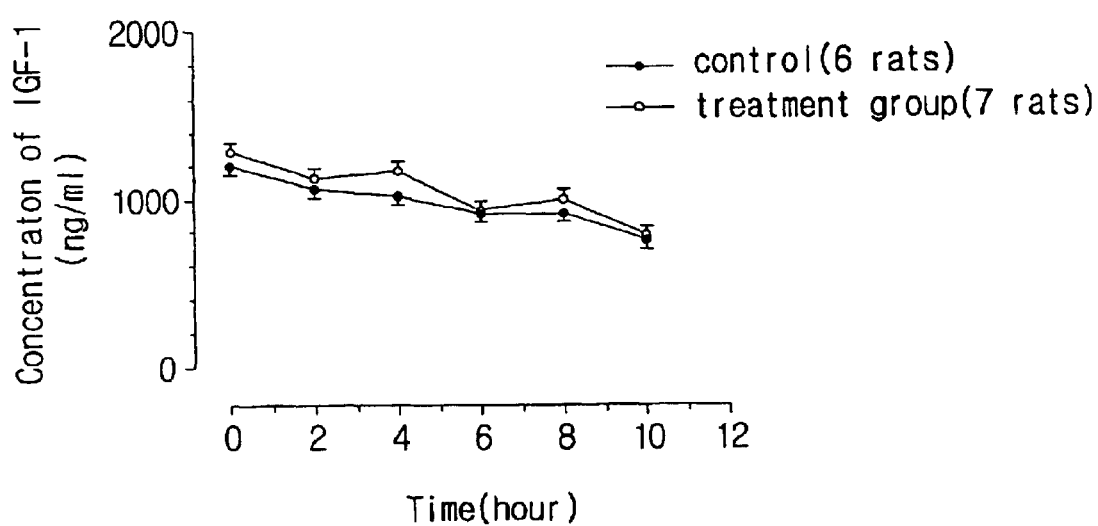
Figure 1D:
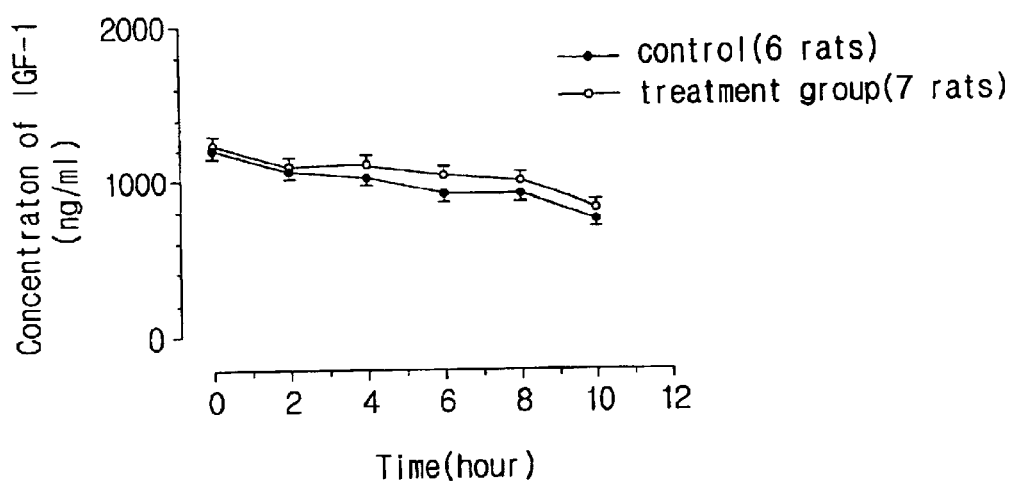

In one aspect of this invention, there is provided a pharmaceutical composition for treating or preventing a disorder associated with reduced serum insulin-like growth factor-1 level, which comprises (a) a pharmaceutically effective amount of an extract obtained from oriental pharmaceutical selected from the group consisting of *Phlomris umbrosa Turez, Cynanchum wilfordii(Max) Hem&ley, Zingiber officinale Rosc., Platycodi Radix* and combination thereof; and (b) a pharmaceutical acceptable carrier, wherein the extract as active ingredient induces secretion of insulin-like growth factor-1.

In another aspect of this invention, there is provided a food composition for inducing secretion of insulin-like growth factor-1, which comprises, as active ingredient, an extract obtained from oriental pharmaceutical selected from the group consisting of *Phlomis umbrosa Turez, Cynanchum wilfordii(Max) Hem&ley, Zingiber officinale Rosc., Platycodi Radix* and combination thereof.

The present compositions capable of inducing secretion of IGF-1 can ameliorate various disorders or diseases associated with reduced serum IGF-1 level. For example, the compositions are found to improve body composition, insulin sensitivity, bone mineral density and linear growth; to inhibit mental retardation, microcephaly, sensorineural deafness and femoral bone loss in postmenopausal women; to stimulate neural stem cell proliferation; and to prevent poor muscle strength and mobility in older women. Furthermore, the present compositions can facilitate linear growth in young men who are poor in growth.

The present inventor has focused on oriental pharmaceuticals to screen candidates for inducing IGF-1, since oriental pharmaceuticals have been already proved to exhibit safety to human, which is confirmed through several facts: (a) oriental pharmaceuticals are derived from natural source, generally, plants, and (b) have been conventionally employed as pharmaceuticals. Through screening a wide variety of oriental pharmaceuticals for inducing IGF-1, *Phlomis umbrosa Turez, Cynanchum wilfordii(Max) Hem&ley, Zingiber officinale Rosc.* and *Platycodi Radix* have been proved to exhibit considerable ability to induce IGF-1.

Among the raw materials, *Phlomis umbrosa Turez* is a perennial plant with typical height of 1 m and has been known to have pharmacological efficacy in protection of liver and kidney. *Cynanchum wilfordii(Max) Hem&ley* is a perennial plant and has been employed to treat or prevent anemia, astriction, ulcer and the like in the Oriental countries such as Korea and China. *Zingiber officinale Rosc.* is a kind of plant belonged to Zingiberaceae and has been reported in the Oriental countries to have pharmacological efficacy including prevention of vomiting, relief of pains and prevention of aggregation of platelet.

*Platycodi Radix* is generally meant to a root of *Platycodon grandiflorum* (Jacq.)A,. DC. belonged to Campanulaceae and has been known in the Oriental countries to exhibit antitussive and pectoral efficacy.

The present inventor has found novel use of the above-described oriental pharmaceuticals to induce or stimulate secretion of IGF-1 in vivo.

Meanwhile, the process for preparing extracts from the oriental pharmaceuticals incorporated into compositions of this invention must be provided in consideration of isolation of active ingredients with significant purity. In particular, the process of this invention must be designed to allow cost-effectiveness, and maintenance and evaluation of physiological activity of the resulting extract. Since the oriental pharmaceuticals used in this invention are highly expensive, the cost-effectiveness of the process appears to be very important factor to be considered.

In this regard, the present inventor has developed a novel process for preparing extracts from the oriental pharmaceuticals, which permits the extracts to be prepared in a cost-effective and massive manner while loss of active ingredients in the oriental pharmaceuticals may be negligible. Furthermore, although the process is very simple, it is significantly effective in preparing extracts.

According to preferred embodiment of this invention, the extract to be incorporated into the present compositions is prepared in accordance with the process comprising the steps of (a) extracting oriental pharmaceutical selected from the group consisting of *Phlomis umbrosa Turez, Cynanchum wilfordii(Max) Hem&ley, Zingiber officinale Rosc., Platycodi Radix* and combination thereof with hot water, whereby a crude extract is obtained; and (b) filtering the crude extract by means of ultrafiltration membrane with molecular weight cut off of 30,000–100,000.

The first extraction employs water as extraction solvent in order to avoid the contamination of the final product by harmful substances to human. Therefore, according to preferred embodiment of this invention, organic solvents such as methanol are not employed.

It is preferable that the hot water employed in first extraction has a temperature ranging from 60° C. to 95° C. If the temperature is lower than 60° C., the extraction of active ingredients for inducing secretion of IGF-1 may be far poor; while if the temperature is higher than 95° C., active ingredients may be destroyed or disrupted in accelerated manner. More preferably, the hot water has a temperature ranging from 80° C. to 90° C. According to preferred embodiment of this invention, the crude extract thus yielded is then cooled, and is subject to centrifugation or paper filtration to remove precipitate.

Thereafter, the resulting crude extract is separated on the basis of molecular weight, finally obtaining desired extract containing active ingredients with relatively low molecular weight. According to this invention, the separation according to molecular weight is carried out by filtration using ultrafiltration membrane with certain molecular weight cut off range. Among various methods, the present inventor has proved that the filtration using ultrafiltration membrane is the most preferable in view of various considerable factors including yield, convenience and cost-effectiveness.

The ultrafiltration membrane used in this invention has typically molecular weight cut off ranging from 30,000 to 100,000. If molecular weight cut off is lower than 30,000, the separation may require much longer time so that cost-effectiveness of the process may be far poor. If molecular weight cut off is more than 100,000, the separation of active ingredients with low molecular weight from molecules with high molecular weight may be negligible so that the relative purity of the final extract may be too low. According to preferred embodiment of this invention, the ultrafiltration membrane has a molecular weight cut off ranging from 50,000 to 100,000.

In preferred embodiment of this invention, the extract thus obtained is concentrated to prepare high concentrated extract. The concentration is performed according to various methods known to one skilled in the art, for example, heating in reduced pressure. If necessary, the concentrated extract is processed to give powder by means of various methods known to one skilled in the art, for example, drying in reduced pressure.

As described above, the process for preparing desired extract can be carried out with feasibility and cost-effectiveness and allow to obtain active ingredients for inducing secretion of IGF-1 with high purity and yield.

According to preferred embodiment of this invention, if necessary, the present composition further comprises calcium, arginine, lysine and/or carboxymethyl cellulose. Calcium is main mineral component of bone, arginine may allow to enhance secretion of growth hormone in body, lysine may promote the action of arginine and carboxymethyl cellulose may prevent wetting to inhibit growth of microorganisms and may facilitate homogeneous mixing of several ingredients in a composition. More preferably, the amount of calcium is 65–80 parts by weight, the amount of arginine is 25–40 parts by weight, the amount of lysine is 5–20 parts by weight and the amount of carboxymethyl cellulose is 2–8 parts by weight based on 100 parts of extract from oriental pharmaceuticals.

In the pharmaceutical compositions of this invention, the pharmaceutically acceptable carrier may be conventional one for formulation, including carbohydrates (e.g., lactose, amylose, dextrose, sucrose, sorbitol, mannitol, starch), gum acacia, calcium phosphate, alginate, gelatin, calcium silicate, microcrystalline cellulose, polyvinylpyrrolidone, cellulose, water, salt solutions, alcohols, gum arabic, syrup, vegetable oils (e.g., corn oil, cotton-seed oil, peanut oil, olive oil, coconut oil), polyethylene glycols, methyl cellulose, methylhydroxy benzoate, propylhydroxy benzoate, talc, magnesium stearate and mineral oil, but not limited to. The pharmaceutical compositions of this invention, further may contain wetting agent, sweetening agent, emulsifier, buffer, suspending agent, preservatives, flavors, perfumes, lubricant, stabilizer, or mixtures of these substances.

It is especially preferred that the pharmaceutical compositions of this invention are orally administered. The compositions of this invention are very effective in treating or prevention various disorders and diseases associated with reduced serum IGF-1 level, especially, improving body composition and week constitution, and preventing osteoporosis and aging.

The pharmaceutical composition of this invention can stimulate or induce secretion of IGF-1 so that it permits treatment of growth failure, facilitation of linear growth in young men, improvement of bone mineral density (prevention and treatment of osteoporosis), prevention of aging, improvement of body composition, treatment of femoral bone loss in postmenopausal women and protection of neural cells.

The correct dosage of the pharmaceutical compositions of this invention will be varied according to the particular formulation, the mode of application, age, body weight and sex of the patient, diet, time of administration, condition of the patient, drug combinations, reaction sensitivities and severity of the disease. It is understood that the ordinary skilled physician will readily be able to determine and prescribe a correct dosage of this pharmaceutical compositions. An exemplary daily dosage unit for human host comprises an amount of from about 5 mg/kg to about 100 mg/kg.

According to the conventional techniques known to those skilled in the art, the pharmaceutical compositions of this invention can be formulated with pharmaceutical acceptable carrier and/or vehicle as described above, finally providing several forms including a unit dosage form. Non-limiting examples of the formulations include, but not limited to, a solution, a suspension or an emulsion, an extract, an elixir, a powder, a granule, a tablet, a capsule, emplastra, a liniment, a lotion and an ointment.

In a food composition of this invention, it can comprise typical ingredients incorporated in food products known to one skilled in the art. Typical food ingredients will include protein, carbohydrates, fats, nutrients and flavors. Preferred food products are drinks, concentrated drinks and instant drinks comprising e.g. citric acid, aqueous fructose, sucrose, glucose, acetic acid and/or fruit juice. Another preferred food products are in the form of powder comprising e.g. essential amino acids such as lysine, arginine, ornithine, glycine and tryptophan, niacin or gamma-hydroxy butyrate.

The following specific examples are intended to be illustrative of the invention and should not be construed as limiting the scope of the invention as defined by appended claims.

EXAMPLE I

Preparation of Extracts from Oriental Pharmaceuticals Containing Active Ingredients with Low Molecular Weight Oriental pharmaceuticals including *Phlomis umbrosa Turez*, *Cynanchum wilfordii(Max) Hem&ley*, *Zingiber officinale Rosc.* and *Platycodi Radix* were purchased in Gyeongdong Market (Seoul, Korea) and used as raw materials.

I-1. Extract from *Phlomis umbrosa Turez*

To 50 g of dried *Phlomis umbrosa Turez*, 1.5 liters of distilled water were added, followed by heating for 2 hr. at 80–90° C. for extraction, thereby obtaining 0.7 liter of aqueous extract. Then, half volume of distilled water used in the first extraction was added to remained *Phlomis umbrosa Turez*, followed by heating for 2 hr. at 80–90° C. for extraction. The extracts obtained in the first and second extraction were combined to collect 1 liter of extract and then heated at 90° C. to concentrate, obtaining final volume of 500 ml.

500 ml of the extract was centrifuged at 3000 x g for 10 min., after which for filtration the supernatant obtained was passed through ultrafiltration membrane with molecular weight cut off (MWCO) of 50,000 or 100,000 by means of stirred cell apparatus (purchased from Amicon, USA). The nitrogen gas pressure used was fixed at 3 atm.

Meanwhile, when the ultrafiltration membrane was blocked, it was replaced by fresh membrane for sequential filtration. The blocked membrane was able to reuse by washing with 0.1 N NaOH and 20% ethanol.

For evaluating the extraction efficiency, the extract obtained at each step was dried under reduced pressure to give powder (Freeze dryer, Edwards USA), and the efficiency was calculated based on weight of powder (see Table 1).

TABLE 1

| Step | Weight (g) | Extraction Efficiency (%) |
| --- | --- | --- |
| Raw materials | 50 | 100 |
| Heating and extracting | 19.5 | 39 |
| Filtration with MWCO of 50,000 | 16.7 | 33.54 |
| Filtration with MWCO of 100,000 | 18.5 | 37 |

The extraction efficiency from step of heating and extracting was slightly varied in several rounds of experiments and usually shown 38%–45%. It is appreciated that lower than 100,000 of molecular weight cut off of ultrafiltration membrane is preferable in view of extraction efficiency and purity of active ingredient capable of induction of secretion of IGF-1.

I-2. Extract from *Cynanchum wilfordii(Max) Hem&ley*

The extract from *Cynanchum wilfordii(Max) Hem&ley* was prepared in the same manner as in Example I-1, except that 50 g of *Cynanchum wilfordii(Max) Hem&ley* were used instead of 50 g of *Phlomis umbrosa Turez*. The extraction efficiency was calculated based on weight of powder (see Table 2).

TABLE 2

| Step | Weight (g) | Extraction Efficiency (%) |
|---|---|---|
| Raw materials | 50 | 100 |
| Heating and extracting | 15 | 30 |
| Filtration with MWCO of 50,000 | 9 | 18 |
| Filtration with MWCO of 100,000 | 11 | 22 |

As demonstrated in Table 2, it is understood that lower than 100,000 of molecular weight cut off of ultrafiltration membrane is preferable in light of extraction efficiency and purity of active ingredient capable of induction of secretion of IGF-1.

I-3. Extract from *Zingiber officinale Rosc.*

The extract from *Zingiber officinale Rosc.* was prepared in the same manner as in Example I-1, except that 50 g of *Zingiber officinale Rosc.* were used instead of 50 g of *Phlomis umbrosa Turez*. The extraction efficiency was calculated based on weight of powder (see Table 3).

TABLE 3

| Step | Weight (g) | Extraction Efficiency (%) |
|---|---|---|
| Raw materials | 50 | 100 |
| Heating and extracting | 9.5 | 19 |
| Filtration with MWCO of 50,000 | 2 | 4 |
| Filtration with MWCO of 100,000 | 3 | 6 |

As indicated in Table 3, the extraction from *Zingiber officinale Rosc.* is shown lower efficiency than *Phlomis umbrosa Turez* and *Cynanchum wilfordli(Max) Hem&ley*. In addition, it is understood that lower than 100,000 of molecular weight cut off of ultrafiltration membrane is preferable in view of extraction efficiency and purity of active ingredient capable of induction of secretion of IGF-1.

I-4. Extract from *Platycodi Radix*

The extract from *Platycodi Radix* was prepared in the same manner as in Example I-1, except that 50 g of *Platycodi Radix* were used instead of 50 g of *Phlomis umbrosa Turez*. The extraction efficiency was calculated based on weight of powder (see Table 4).

TABLE 4

| Step | Weight (g) | Extraction Efficiency (%) |
|---|---|---|
| Raw materials | 50 | 100 |
| Heating and extracting | 9.5 | 19 |
| Filtration with MWCO of 50,000 | 4.3 | 8.5 |
| Filtration with MWCO of 100,000 | 5.5 | 11 |

As indicated in Table 4, the extraction from *Platycodi Radix* is shown lower efficiency than *Phlonis umbrosa Turez* and *Cynanchum wilfordii(Max) Hem&ley*. In addition, it is understood that lower than 100,000 of molecular weight cut off of ultrafiltration membrane is preferable in view of extraction efficiency and purity of active ingredient capable of induction of secretion of IGF-1.

In conclusion, the extracts containing active ingredient capable of induction of secretion of IGF-1 are prepared in effective and feasible manner from *Phlomis umbrosa Turez, Cynanchum wilfordii(Max) Hem&ley, Zingiber officinale Rosc.* or *Platycodi Radix,* which comprises the steps of (a) extracting with hot water, and (b) filtering by means of ultrafiltration membrane with molecular weight cut off of 30,000–100,000. In addition, the temperature of hot water in extraction is preferred to be 80° C. to 90° C. and MWCO of the ultrafiltration membrane used in filtration is preferred to be 50,000 to 100,000.

EXAMPLE II

Induction of Secretion of IGF-1 by Extracts

The samples to be administered were prepared in such a manner that 252 mg of the powder, which is obtained using ultrafiltration membrane with MWCO of 50,000 as described in Example I, were dissolved in 1 ml of distilled water. Animals employed were male Sprague Dawley rat with age of 9 weeks, weighed about 300 g. The experimental animals were fasted for 1 day prior to administration, because the sensitivity to stimulus to secretion of IGF-1 is increased. The number of control group and treated group was 6 and 7, respectively.

1000 $\mu$l of extracts were orally administered to rats using syringe for oral administration. Collecting blood samples from heart was performed prior to administration, and then at 2 hr, 4 hr, 6 hr, 8 hr and 10 hr after administration, respectively. It is notable that any anesthetics were not used during experiment because they may affect secretion pattern of IGF-1.

Thereafter, IGF-1 in the collected blood samples was quantified using enzyme immunoassay kit (Diagnostic System Laboratory, USA) according to manufacturer's protocol, of which results are shown in FIGS. 1a–1d.

As demonstrated in FIGS. 1a–1d, from 4 hours after administration, the group treated with the extract from *Phlomis umbrosa Turez, Cynanchum wilfordii(Max) Hem&ley, Zingiber officinale Rosc.* or *Platycodi Radix* shows significantly higher concentration of IGF-1 in serum than control group. Therefore, it is understood that the extracts of this invention are effective in increasing IGF-1 level in serum. In addition, as indicated in FIGS. 1a–1d, it is known that level of IGF-1 in serum is maximized from 8 hours after administration.

EXAMPLE III

Evaluation on Bone Formation by Extracts

The feed to be administered was prepared using the powder which was obtained using ultrafiltration membrane with MWCO of 50,000 as described in Example I. The composition of feed is described in Tables 5 and 6.

TABLE 5

| Ingredients | Amount (mg) |
|---|---|
| Extract from *Phlomis umbrosa Turez* | 50 |
| Calcium from marine algae | 37.5 |
| Arginine | 16.8 |
| Lysine | 5.6 |
| Carboxymethyl cellulose | 2.25 |

TABLE 6

| Ingredients | Amount (mg) |
|---|---|
| Extract from *Cynanchum wilfordii* (Max) Hem&ley | 15 |
| Extract from *Zingiber officinale* Rosc. | 15 |
| Extract from *Platycodi Radix* | 20 |
| Calcium from marine algae | 37.5 |
| Arginine | 16.8 |
| Lysine | 5.6 |
| Carboxymethyl cellulose | 2.25 |

The total weight of feed was 15 g and other ingredients used conventionally for animal feed were also incorporated into the feed.

Animals employed were male Sprague Dawley rat with age of 3 weeks. The experimental animals were subject to long-term feeding (for 8 weeks) with the above-described feed, and then were anesthetized with ethyl ether and sacrificed, after which femur and/or tibia were extracted and then length of them was measured. The number of control group and experimental group was 4. The control group was fed with feed not containing extract of this invention.

Figure 2A:
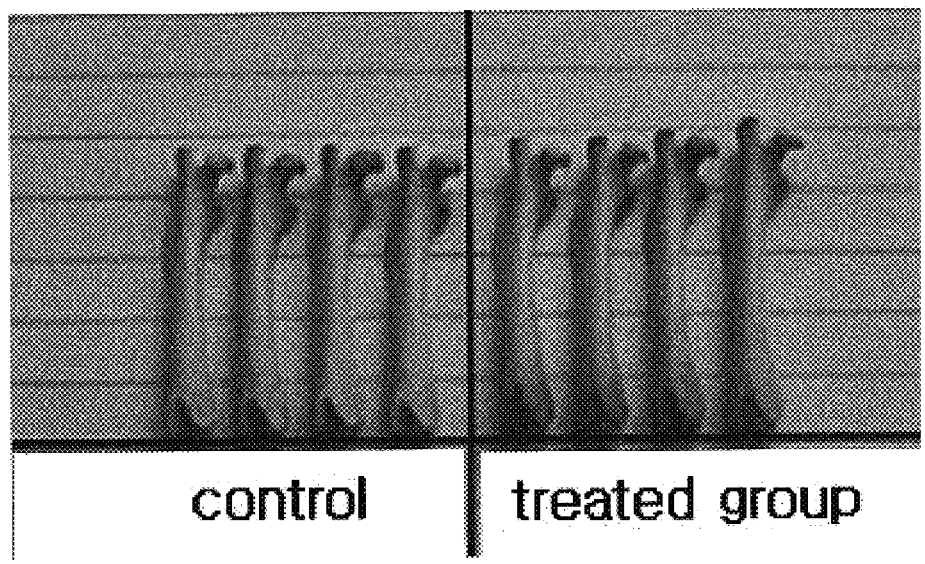
FIGS. 2a and 2b are photographs showing an increase of length of femur (FIG. 2a) and tibia (FIG. 2b) in rats administered with composition comprising the extracts from *Phlomis umbrosa Turez;*
Figure 2B:
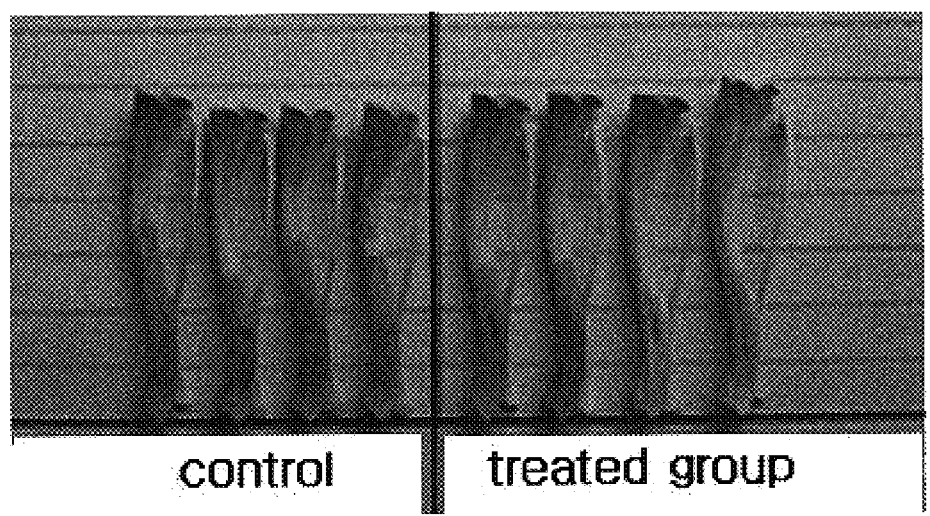
Figure 3:
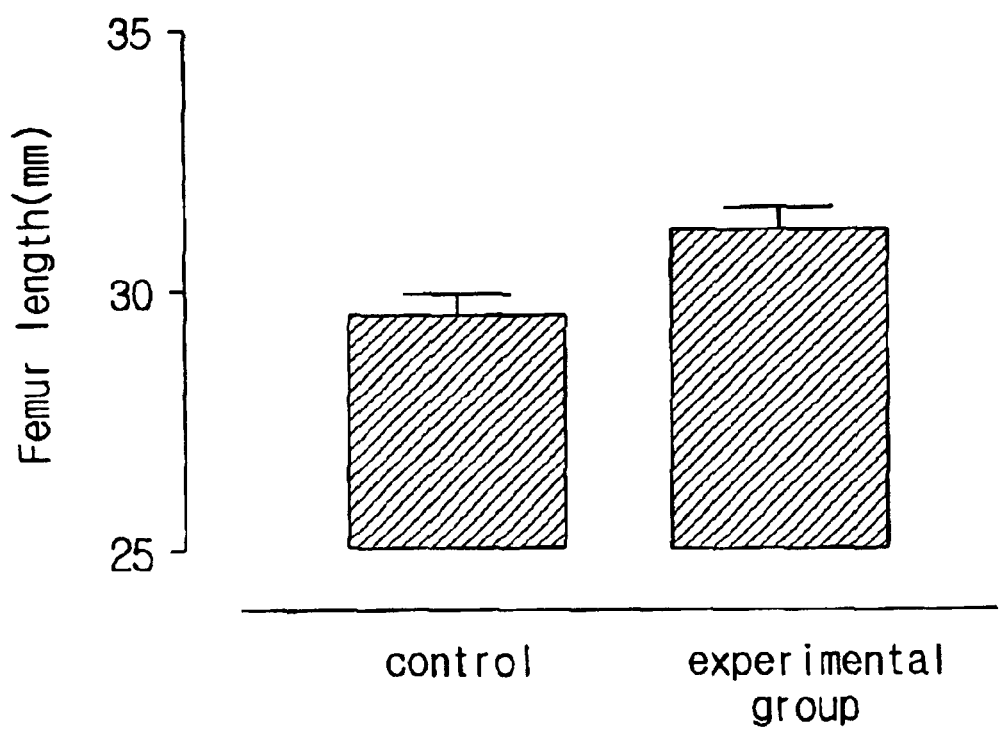
FIG. 3 is a graph representing an increase of length of femur in rats administered with composition comprising the extracts from *Phlomis umbrosa Turez.

As demonstrated in FIGS. 2a–2b and 3, the experimental animals treated with the feed containing extract from *Phlomis umbrosa Turez*, were found to have much longer femur and the tibia than control group. Therefore, it is confirmed that the extract from *Phlomis umbrosa Turez* is able to stimulate bone formation, thus leading to facilitation of linear growth.

Figure 4:
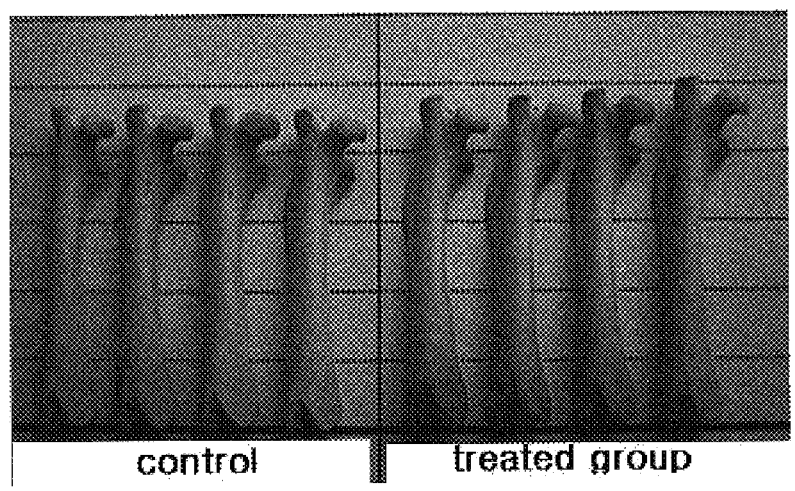
* and FIG. 4 is a photograph showing an increase of length of femur in rats administered with composition comprising the extracts from *Cynanchum wilfordii(Max) Hem&ley, Zingiber officinale Rosc.* and *Platycodi Radix*.

In addition, as observed in FIG. 4, the experimental animals treated with the feed containing extracts from *Cynanchum wilfordii*(Max) Hem&ley, *Zingiber officinale* Rosc. and *Platycodi Radix*, were found to have much longer femur than control group. Therefore, it is understood that the extracts from *Cynanchum wilfordii*(Max) Hem&ley, *Zingiber officinale* Rosc. and *Platycodi Radix* can stimulate bone formation, thereby leading to facilitation of linear growth.

Preparative Example 80 ml of extract obtained using ultrafiltration membrane with MWCO of 50,000 as described in Example I, 10 ml of aqueous fructose, 0.5 ml of citric acid and 9.5 ml of extract from licorice root were homogeneously mixed to prepare drink product.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A food composition for inducing secretion of insulin-like growth factor-1, which comprises, as active ingredient, an extract obtained from *Phlomis umbrosa Turcz*; in which the extract is prepared by a process comprising the steps of (i) extracting *Phlomis umbrosa Turcz* with hot water, whereby a crude extract is obtained; and (ii) filtering the crude extract by means of an ultrafiltration membrane with molecular weight cut off of 30,000–100,000.

2. The composition according to claim 1, wherein the hot water has a temperature ranging from 60° C. to 95° C.

3. The composition according to claim 2, wherein the hot water has a temperature ranging from 80° C. to 90° C.

4. The composition according to claim 1, wherein the ultrafiltration membrane has a molecular weight cut off ranging from 50,000 to 100,000.

5. The composition according to claim 1, wherein the composition has an activity of stimulating bone formation.

6. The composition according to claim 1, wherein the composition has an activity of preventing bone loss.

7. A pharmaceutical composition comprising a pharmaceutically effective amount of an extract obtained from *Phlomis umbrosa Turcz* and a pharmaceutically acceptable carrier, wherein the extract as active ingredient induces secretion of insulin-like growth factor-1, and wherein the extract is prepared by a process comprising (i) extracting *Phlomis umbrosa Turcz* with hot water to obtain a crude extract and (ii) filtering the crude extract by means of an ultrafiltration membrane having a molecular weight cutoff of 30,000 to 100,000.

* * * * *